United States Patent [19]

Hiroshima et al.

[11] 4,127,813
[45] Nov. 28, 1978

[54] METHOD FOR BALANCING THE SENSITIVITY OF TWO CHANNELS IN A DIFFERENTIAL DETECTION APPARATUS

[75] Inventors: Tatsuo Hiroshima; Tetsuya Hirota, both of Amagasaki, Japan

[73] Assignee: Sumitomo Metal Industries, Ltd., Osaka, Japan

[21] Appl. No.: 797,853

[22] Filed: May 17, 1977

[30] Foreign Application Priority Data

May 24, 1976 [JP] Japan .............................. 51/060292

[51] Int. Cl.² ........................................... G01R 33/12
[52] U.S. Cl. ................................... 324/202; 324/238; 307/353; 307/355; 328/147; 328/168; 73/618; 250/214 AG
[58] Field of Search ................... 324/37, 40, 202, 225, 324/238, 243, 74, 130; 307/264, 353, 355; 328/146, 147, 168, 173, 175; 73/1 DV, 67.8 S, 599, 618, 625; 250/214 AG

[56] References Cited

U.S. PATENT DOCUMENTS

| | | | |
|---|---|---|---|
| 3,714,441 | 1/1973 | Kreda ........................... | 250/214 AG |
| 3,986,037 | 10/1976 | Faulhaber ..................... | 250/214 AG |
| 3,999,133 | 12/1976 | Lee et al. ..................... | 307/264 |
| 4,037,163 | 7/1977 | Nicholas ........................ | 307/264 |

*Primary Examiner*—Robert J. Corcoran
*Attorney, Agent, or Firm*—Wenderoth, Lind & Ponack

[57] ABSTRACT

A method is provided for balancing the sensitivity of two channels comprising intermittently-appearing pulse waves, such as the signals generated by respective sensors in a detecting couple which is used in the so-called differential detection of flaws in materials. The balancing of the levels of the pulse signals is accomplished by the use of, essentially, a pair of sample and hold circuits, one or two variable gain amplifiers and the same number of comparison loops as variable gain amplifiers.

3 Claims, 3 Drawing Figures

METHOD FOR BALANCING THE SENSITIVITY OF TWO CHANNELS IN A DIFFERENTIAL DETECTION APPARATUS

BACKGROUND OF THE INVENTION

1. Field of the Invention

This invention relates to a method for balancing the sensitivity of two channels comprising intermittently-appearing pulse waves.

More particularly, the invention relates to a method of balancing the sensitivity of two channels comprising intermittently-appearing pulse waves, such as the signals generated by respective sensors in a detecting pair which is used in the so-called differential detection of flaws in materials.

2. Description of the Prior Art

In nondestructive testing apparatus such as a magnetic flaw detector or an ultrasonic flaw detector, the principle generally employed is that of differential flaw detection in which a pair of detecting means are caused to scan the same part of the test material at a suitable time interval and the output pulse signals generated by these two detecting means are differentially amplified to improve the detection sensitivity of the apparatus. To accomplish the desired object with such differential detection, the peak values of the flaw signals, i.e. the pulse waves corresponding to any single flaw in the test material, must be identical. While the above conditions are met when the two detecting means have the same sensitivity, it is practically impossible to manufacture two detecting means having exactly the same sensitivity. For this purpose, it is conventional practice to adjust the gains of the preamplifiers provided in the instrument to which these detecting means are directly connected so as to compensate for the difference existing in sensitivity between the two detecting means. This sensitivity compensation is carried out as follows. Thus, a control reference standard which is identical in material and shape with the material to be tested and which has been artificially given a multiplicity of standardized flaws is scanned with the aforementioned two detecting means and the necessary sensitivity compensation is accomplished by the use of the two pulse output signals of the detecting means. However, because the flaw signals corresponding to the flaws on the control reference standard appear only intermittently, the output of the preamplifier is difficult to monitor and, therefore, there are experienced such disadvantages as an inaccurate sensitivity compensation and the prolonged time required for adjustments for obtaining the necessary compensation.

This invention has been accomplished to obviate the foregoing disadvantages. Thus, the invention has as its object to provide means for balancing the levels of two pulse signals, which can be utilized for the compensation for sensitivity differences as noted above, which means comprises causing the peak values of pulse waves in the pulse signals to be held by a sample and hold circuit for an appropriate period of time and, during that time, causing the gain of a variable gain amplifier to be automatically adjusted. This invention will hereinafter be described in detail, reference being had to the accompanying drawing.

SUMMARY OF THE INVENTION

A method of balancing the levels of peaks of a pair of pulse signals comprising intermittently-appearing pulse waves, which comprises feeding the two pulse signals to two sample and hold circuits, respectively, each of the sample and hold circuits being adapted to hold the peak value of the input signal for an appropriate time, feeding the output signals of the two sample and hold circuits, one directly and the other indirectly through a variable gain amplifier or both through respective variable gain amplifiers, to a comparator and feeding the output signal of a power amplifier connected to the output of said comparator back to said variable gain amplifier or amplifiers so that the gain function of said variable gain amplifier will be automatically adjusted to cause the output signal of said power amplifier to be equal to zero.

BRIEF DESCRIPTION OF THE DRAWING

In the accompanying drawing which illustrate, an embodiment of this invention.

DESCRIPTION OF AN EMBODIMENT OF THE INVENTION

Figure 1:
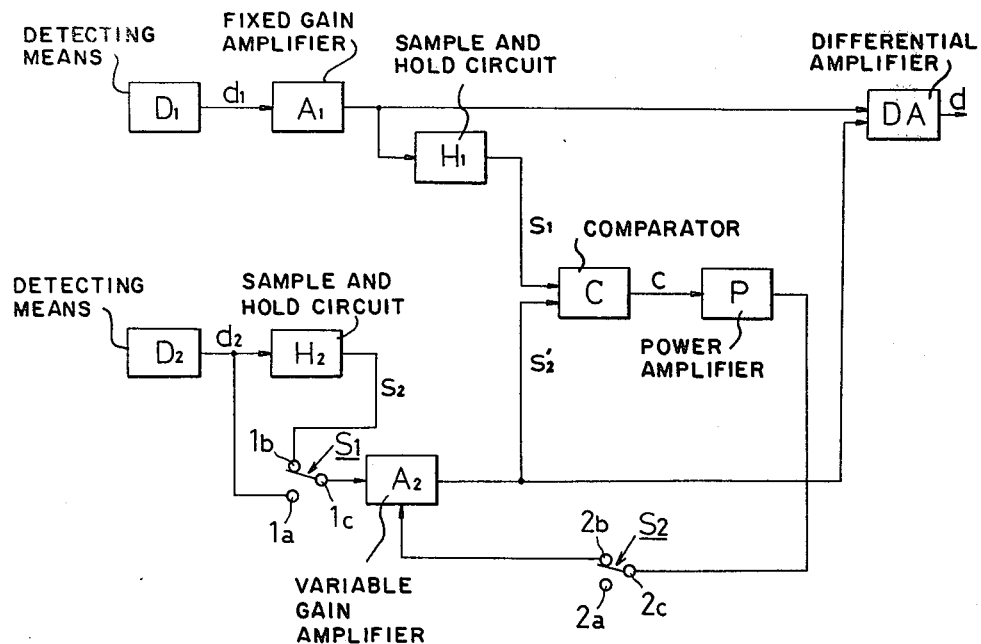
FIGS. 1 and 3 show the block diagrams of an electronic circuit which is employed when the method of this invention is utilized for the sensitivity compensation of a magnetic flaw detecting apparatus.

When the method of this invention is utilized for the sensitivity compensation of a magnetic flaw detection apparatus, there is used an electronic circuit such as that shown by the block diagram of FIG. 1.

Referring to FIG. 1, $D_1$ and $D_2$ stand for the detecting means, respectively. The detecting means $D_1$ is connected to a comparator C through a fixed gain amplifier $A_1$ and a sample and hold circuit $H_1$ which is adapted to sample the peak value of the input signal and hold it for an appropriate time. The detecting element $D_2$ is connected directly to a terminal 1a of a switch $S_1$ and indirectly to the other terminal 1b of said switch $S_1$ through a sample and hold circuit $H_2$ similar to the sample and hold circuit $H_1$. The switch $S_1$ further has a common terminal 1c which is connected to the comparator C through a variable gain amplifier $A_2$. The output of the comparator C is connected to a common terminal 2c of a switch $S_2$ through a power amplifier P, with one switch terminal 2b of the switch $S_2$ being connected to the gain control terminal of the variable gain amplifier $A_2$, while the other switch terminal 2a remains unconnected. The outputs of the fixed gain amplifier $A_1$ and the variable gain amplifier $A_2$ are respectively connected to a differential amplifier DA located within the magnetic flaw detecting apparatus.

In operation, the switches $S_1$ and $S_2$ are switched to the terminals 1b and 2b, respectively, and the detecting means $D_1$ and $D_2$ are caused to scan the aforesaid control reference standard. Because the detecting means $D_1$ and $D_2$ are so disposed that they will scan the same part of the control reference standard at a suitable time interval, the flaw signal $d_1$ generated by the detecting means $D_1$ in response to a flaw in the control reference standard and the corresponding flaw signal $d_2$ generated by detecting means $D_2$ will be as indicated in (a) and (b) of FIG. 2. Thus, the maximum value of flaw signal $d_1$ and the minimum value of flaw signal $d_2$ appear in temporal coincidence, that is to say the flaw signal $d_2$ appears with a delay of a half-cycle from the flaw signal $d_1$, with the peak values $e_1$ and $e_2$ being different, e.g. $e_1 > e_2$, because of the difference in sensitivity between the detecting means $D_1$ and $D_2$ as mentioned hereinbefore.

The flaw signal $d_1$ is fed to the input of the fixed gain amplifier $A_1$, where the peak values $e_1$ of flaw signal $d_1$ is amplified to $E_1$. However, since this peak value $E_1$ is held in the sample and hold circuit $H_1$, a sample signal $S_1$ like that illustrated in (c) of FIG. 2 is fed to the input of the comparator C from the sample and hold circuit $H_1$.

Figure 2:
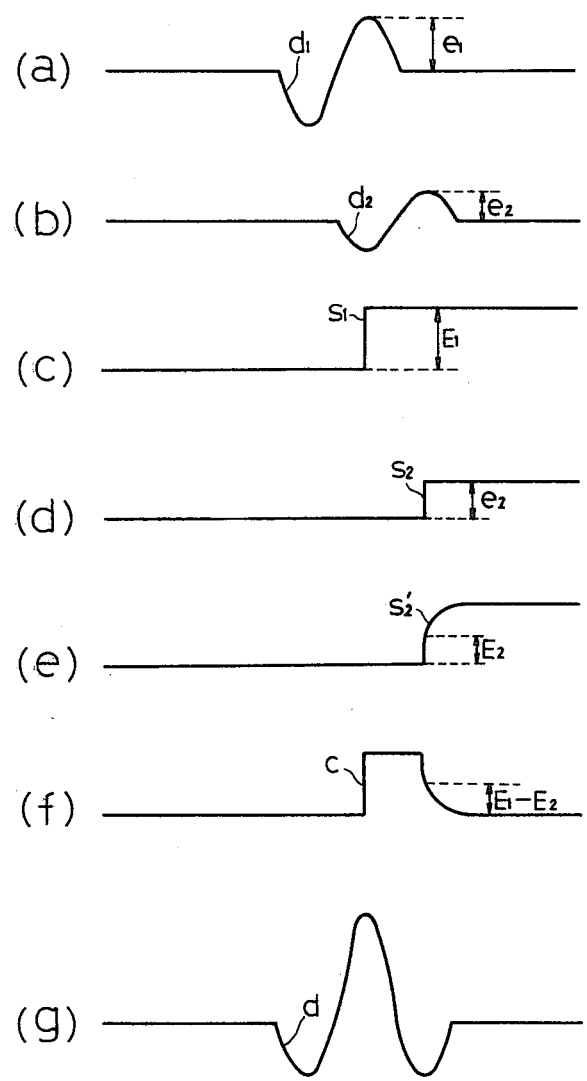
FIG. 2 is a wave-form diagram showing the waveforms of signals in the various parts of the circuit shown in FIG. 1.

On the other hand, the peak value $e_2$ of flaw signal $d_2$ is not preamplified but is directly held by the sample and hold circuit $H_2$, with the result that a sample signal $s_2$ like that shown in (d) of FIG. 2 is fed to the input of the variable gain amplifier $A_2$ from the sample and hold circuit $H_2$. Therefore, the variable gain amplifier $A_2$ amplifies the sample signal $s_2$ at a gain which is dictated by the initial amplifier condition so that the comparator C receives a sample signal $s_2'$ having the initial voltage level $E_2$ [See FIG. 2(e)] corresponding to the aforesaid peak value $e_2$.

The output of the comparator C is equal to the difference between the two input signals, $s_1-s_2$, but as mentioned hereinbefore, because the flaw signal $d_2$ appears with a delay of a half-cycle from the flaw signal $d_1$, the rise times of the sampling signals $s_2'$ and $s_1$ are also different by a half-cycle in correspondence with the differential times of occurence of the respective peaks $e_2$ and $e_1$, with the result that the output signal c of the comparator C will assume a wave-form like the one shown in (f) of FIG. 2. Since this output signal c is amplified by the power amplifier P and fed back to the gain control terminal of the variable gain amplifier $A_2$, the gain of the variable gain amplifier $A_2$ changes in the direction for reducing the voltage level $E_1-E_2$ of the output signal c of the comparator C at the time immediately following the moment of input of the sample signal $s_2'$, with the result that the sample signal $s_2'$ which is the output signal of $A_2$ varies gradually at small increments as shown in (e) of FIG. 2. It follows, then, that the voltage level of the output signal c of comparator C after the moment of input of sample signal $s_2'$ undergoes a gradual drop from $E_1-E_2$ and ultimately reaches zero as illustrated in (f) of FIG. 2. In this manner, the level balancing of the flaw signals $d_1$ and $d_2$, that is to say the compensation for difference in sensitivity between detecting elements $d_1$ and $d_2$ is completed.

In the above situation, the detection of flaws in the control standard is made feasible by switching the switches $S_1$ and $S_2$ to terminals 1a and 2a, respectively. By the above scanning of the control reference standard, the detecting elements $D_1$ and $D_2$ generate flaw signals $d_1$ and $d_2$, respectively, which are dictated by the respective flaw detecting sensitivities but since, as aforesaid, the gain of the variable gain amplifier $A_2$ to which the flaw signal $d_2$ is fed through switch $S_1$ has already been adjusted, the differential amplifier DA which is connected to the fixed gain amplifier $A_1$ and variable gain amplifier $A_2$ receives the amplified signals (of flaw signals $d_1$ and $d_2$) having an identical peak value irrespective of the differences in peak value between the flaw signals $d_1$ and $d_2$, with the result that an ideal differential flaw signal d such as that shown in (g) of FIG. 2 is obtained from the differential amplifier DA.

In accordance with the method of this invention, if the sampled and value hold times of the sample hold circuits $H_1$ and $H_2$ are preset to an indefinite time, i.e. until reset, the control reference standard may be preliminarilly scanned only once and, moreover, it is sufficient that only one flaw need be detected by the two detecting means $D_1$ and $D_2$. Thus, the desired compensation for difference in sensitivity may be accomplished in a very short time. Furthermore, since the level balancing for such compensation is accomplished by an automatic adjustment of the gain of the variable gain amplifier $A_2$, the balancing may be achieved with high accuracy, and it no longer happens that the detection of flaws in the test piece is made with low detection sensitivity due to the inadequate compensation occasioned by adjustment errors on the part of the operator as it is often encountered when the prior art method is employed.

Figure 3:
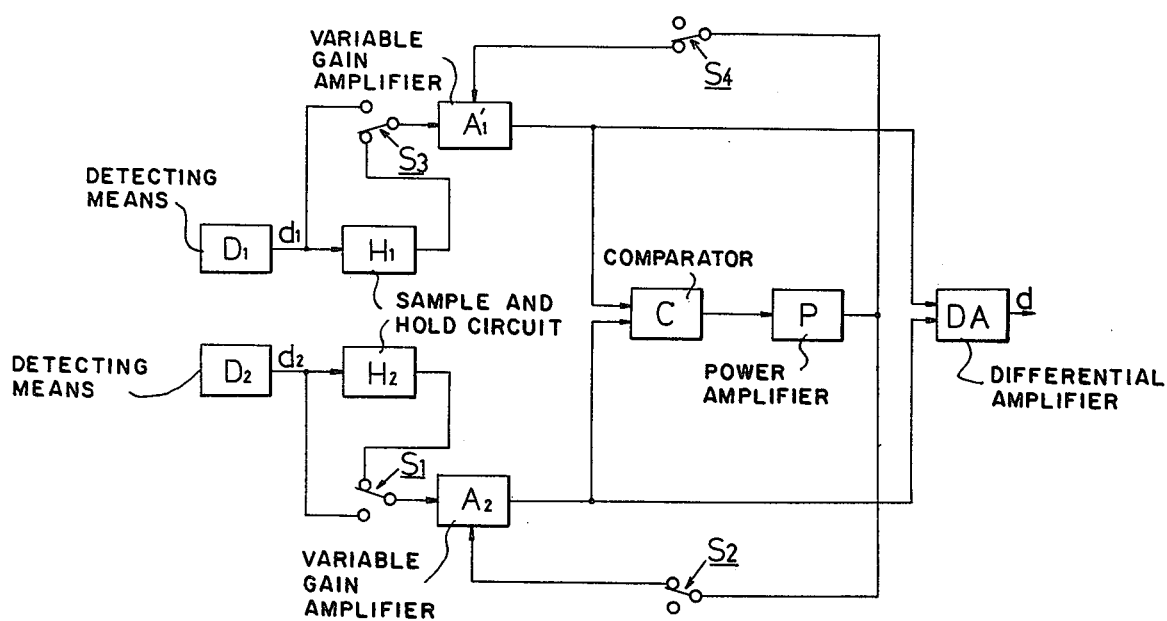

It should be understood that while, in the above embodiment, only one variable gain amplifier is employed, it is of course possible to employ a circuit such as illustrated in FIG. 3 in which the flaw signal $d_1$ of the detecting means $D_1$ is also amplified by a variable gain amplifier $A_1'$.

We claim as our invention:

1. A method for balancing the sensitivity of two channels which ,process intermittently-appearing pulse waves in a differential detection apparatus, said method comprising feeding each of two reference pulse wave signals to respective sample and hold circuits in each channel, each of said sample and hold circuits being adapted to hold the peak value of the input signal for a predetermined time, feeding the respective output signals of said two sample and hold circuits to a comparator, at least one of said output signals being made to pass through a variable gain amplifier, feeding the output signal of said comparator to a power amplifier, and feeding the output signal of said power amplifier back to said at least one variable gain amplifier so that the gain function of said at least one variable gain amplifier will be automatically adjusted to cause the output signal of said power amplifier to be equal to zero.

2. A method for balancing the sensitivity of two channels as set forth in claim 1 wherein said two pulse wave signals are respectively generated by two detecting means of a nondestructive testing apparatus said detecting means being adapted to scan the surface of a material whose flaws are to be detected in identical paths and at a predetermined interval of time.

3. A method for balancing the sensitivity of two channels as set forth in claim 1 wherein the output of each of said sample and hold circuits are made to pass through a respective one of two variable gain amplifiers, and the output of said power amplifier is fed back to each of said variable gain amplifiers to automatically adjust the gain function of said variable gain amplifier.

* * * * *